United States Patent [19]

Foland et al.

[11] Patent Number: 5,710,296

[45] Date of Patent: Jan. 20, 1998

[54] PROCESS FOR PREPARING PHENYL ESTERS

[75] Inventors: LaFayette D. Foland, Dublin; Thomas B. Ottoboni, Belmont, both of Calif.

[73] Assignee: The Clorox Company, Oakland, Calif.

[21] Appl. No.: 450,162

[22] Filed: May 25, 1995

[51] Int. Cl.$^6$ ........................................................ C11C 3/00
[52] U.S. Cl. ............................ 554/167; 554/170; 560/17; 560/130
[58] Field of Search ........................... 584/170, 167; 560/17, 130

[56] References Cited

U.S. PATENT DOCUMENTS

| | | |
|---|---|---|
| 3,996,152 | 12/1976 | Edwards et al. . |
| 4,283,301 | 8/1981 | Diehl . |
| 4,337,213 | 6/1982 | Marynowski et al. . |
| 4,735,740 | 4/1988 | Zielske . |
| 4,778,618 | 10/1988 | Fong et al. . |
| 4,985,180 | 1/1991 | Bellis et al. ........................ 260/404 |
| 5,091,560 | 2/1992 | Rowland . |
| 5,124,475 | 6/1992 | Nepras et al. . |
| 5,182,045 | 1/1993 | Rowland et al. . |
| 5,235,077 | 8/1993 | Amini et al. . |
| 5,391,812 | 2/1995 | Rowland et al. . |

FOREIGN PATENT DOCUMENTS

| | | |
|---|---|---|
| 0105672 | 9/1983 | European Pat. Off. . |
| 0105673 | 9/1983 | European Pat. Off. . |
| 92/16491 | 10/1992 | WIPO . |

*Primary Examiner*—Paul F. Shaver
*Assistant Examiner*—Deborah D. Carr
*Attorney, Agent, or Firm*—Majestic, Parsons, Siebert & Hsue

[57] ABSTRACT

A method for preparing phenyl esters in high yields under mild reaction conditions is provided. Particularly preferred phenyl esters prepared in accordance with the inventive method are alkanyloxy-benzene compounds having a $C_{2-18}$ alkyl. The method is practiced by reacting a carboxylic acid with an acid halide either in the presence of or followed by the addition of a phenol.

15 Claims, No Drawings

5,710,296

PROCESS FOR PREPARING PHENYL ESTERS

FIELD OF THE INVENTION

The present invention generally relates to phenyl esters, useful in applications such as activators for hydrogen peroxide in bleaching and cleaning applications, and more particularly relates to a process for preparing a phenyl ester from a carboxylic acid, a phenol, and an acid halide in good yield.

BACKGROUND OF THE INVENTION

Peroxy compounds are effective bleaching agents, and compositions including mono- or di-peroxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid can present a problem for storage stability for compositions consisting of or including peroxyacids.

One approach to the problem of reduced bleaching activity of peroxyacid compositions has been to include activators of peroxyacids. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester.

U.S. Pat. No. 4,778,618, inventors Fong et al., issued Oct. 18, 1988, provides novel bleaching compositions comprising peracid precursors with the general structure

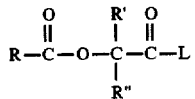

wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_{3\alpha+}$, wherein $R^\alpha$is $C_{1-30}$ alkyl; and where L is a leaving group which can be displaced in a peroxygen bleaching solution by perhydroxide anion. U.S. Pat. Nos. 5,182,045, issued Jan. 26, 1993, and 5,391,812, issued Feb. 21, 1995, inventors Rowland et al., are similar, but are polyglycolates of the Fong et al. monoglycolate precursors, or activators.

U.S. Pat. No. 4,985,180, issued Jan. 15, 1991, inventors Bellis et al., describe the preparation of bleach activator compounds in a two-step process where a phenol derivative is reacted with an α-haloacetyl halide to yield a phenyl ester intermediate followed by reacting the intermediate with a nucleophile. Thus, for example, an intermediate such as 4-(chloroacetyloxy)benzene sulfonic acid, sodium salt, can be prepared from 4-hydroxybenzene sulfonic acid, mixed xylenes, and chloroacetyl chloride in the presence of a tetra-n-butylphosphonium chloride catalyst.

U.S. Pat. No. 5,235,077, issued Aug. 10, 1993, inventors Amini et al., which describes the preparation of activators through reactions of phenyl chloroacetate with a $C_6$–$C_{12}$ carboxylic acid. This patent refers to U.S. application Ser. No. 07/674,401, for a process describing preparation of the phenylchloroacetate. Said U.S. application was published in the form of its corresponding European application, WO92/16491, published Oct. 1, 1992, inventors Dumas et al. In this publication, phenylchloroacetate is prepared by reacting chloroacetyl chloride with phenol in the presence of a catalyst.

New peroxygen activators that provide good bleaching remain desirable for laundry and household bleaching and cleaning applications, and methods for efficiently preparing such activators in high yields are desirable. Activators prepared in accordance with the present invention can be formulated as are described in several copending applications: application Ser. No. 08/449,882, filed concurrently herewith, inventors Scheuing et al., entitled "Liquid Peracid Precursor Colloidal Dispersions: Oil-Core Vesicles;" application Ser. No. 08/450,741, filed concurrently herewith, inventors Scheuing et al., entitled "Liquid Peracid Precursor Colloidal Dispersions: Liquid Crystals;" application Ser. No. 08/452,619, filed concurrently herewith, inventors Van Buskirk et al., entitled "Liquid Peracid Precursor Colloidal Dispersions: Microemulsions;" and application Ser. No. 08/450,740, filed concurrently herewith, inventors Van Buskirk et al., entitled "Liquid Peracid Precursor Colloidal Dispersions: Macroemulsions."

SUMMARY OF THE INVENTION

In one aspect of the present invention, a method of preparing a phenyl ester comprises reacting a carboxylic acid with an acid halide to form an activated intermediate. The activated intermediate is exposed to a phenol to form the phenyl ester. Preferably the phenol is present during the reaction of carboxylic acid with acid halide.

In a particularly preferred embodiment, the carboxylic acid is aliphatic with a $C_{2-18}$ alkyl, the acid halide is chloroacetyl chloride, and the phenol is unsubstituted. Good yields are obtainable by practicing the method. For example, phenyl nonanoate as reaction product can be isolated in greater than about 80% yield.

Among the advantages of the present invention are that one does not need to isolate the activated intermediate in order to make the ester so that a "one pot" synthesis can conveniently be performed. Further, high temperatures are not necessary, since the reaction product is readily formed upon mild heating (e.g. about 70° C.–100° C.) and in a variety of aprotic solvents.

Phenyl esters prepared in accordance with the invention include alkanyloxybenzenes that are capable of activating a peroxide moiety and that are useful as activators in bleaching and cleaning applications.

DETAILED DESCRIPTION OF THE PREFERRED EMBODIMENTS

The present invention is a method for preparing phenyl esters having the Formula I structure below.

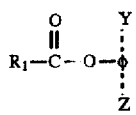

FORMULA I

In the Formula I representation, $R_1$ is an aliphatic or aromatic group, more particularly is a $C_{1-20}$ aliphatic group (e.g. alkyl or alkenyl) or an aryl. Particularly preferred $R_1$ substitutes of the Formula I structure are selected from alkyl groups (branched and unbranched) having 2 to about 12 carbon atoms (ethyl, propyl, butyl, pentyl, hexyl, heptyl, octyl, nonyl, decyl, undecyl, and dodecyl). A most preferred $R_1$ group is where $R_1$ is an octyl group and the compound formed by the inventive process is phenyl nonanoate, which is an excellent bleach activator in certain liquid applications as will be hereinafter exemplified.

In the Formula I structure the dotted lines from the aromatic ring to an Y and to a Z substituent represent the optional presence of one or two substituent(s). Illustrative substituents are described (as Y and Z) in U.S. Pat. No. 5,391,812, incorporated wherein Y and Z are, individually H, $SO_3M$, $CO_2M$, $SO_4M$, OH, halo substituent, $-OR^2$, $R^2$, $NR_3{}^4X$, and mixtures thereof wherein M is an alkali metal or alkaline earth counterion, $R^2$ of the $OR^2$ substituent is $C_{1-20}$ alkyl, $R^3$ is $C_{1-6}$ alkyl, $R^4$ of the $NR_3{}^5$ substituent $C_{1-30}$ alkyl, X is a counterion, and Y and Z can be the same or different.

The alkali metal counterions to sulfonate, sulfate, or carboxy (all of which are solubilizing groups) include $K^+$, $Li^+$ and most preferably, $Na^+$. The alkaline earth counterions include $Sr^{++}$, $Ca^{++}$, and most preferably, $Mg^{++}$. Ammonium ($NH_4$) and other positively charged counterions may also be suitable. The halo substituent can be F, Br or most preferably, Cl. When $-OR^2$, alkoxy, is the substituent on the phenyl ring, $R^2$ is $C_{1-20}$, and the criteria defined for R on the acyl group apply. When $R^3$ is the substituent on the phenyl ring, it is a $C_{1-10}$ alkyl, with preference given to methyl, ethyl, N— and isopropyl, N—, sec- and tert-butyl, which is especially preferred. When $-NR_3{}^4X$ (quaternary ammonium) is the substituent, it is preferred that two of $R^4$ be short chain alkyls ($C_{1-4}$, most preferably, methyl) and one of the $R^4$ alkyls be longer chain alkyl (e.g., $C_{8-30}$), with X, a negative counterion, preferably selected from halogen (Cl—, F—, Br—, I—), $CH_3SO_4$— (methosulfate), $NO_3$—, or OH—.

Especially preferred are phenol sulfonate leaving groups. A preferred synthesis of phenol sulfonate esters which could be adapted for use herein is disclosed in U.S. Pat. No. 4,735,740, inventor Alfred G. Zielske, entitled "Diperoxyacid Precursors and Method" issued Apr. 5, 1988. Preferred phenol derivatives are:

—O—φ—$SO_3M$ (especially sodium o-phenyl sulfonate)

—O—φ—OH (p-, o- or m-dihydroxybenzene)

—O—φ—$C(CH_3)_3$ (t-butyl phenol)

—O—φ—$CO_2H$ (4-oxy-Benzoic Acid) herein by reference.

In order to practice the inventive method, a carboxylic acid having the $R_1$ substituent is reacted with an acid halide having the structure

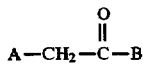

where A is a halide, methoxy, ethoxy, or an electron withdrawing group having an O, N, or S heteroatom and where B is a halide. More preferably, the acid halide is chloroacetyl chloride.

Reaction of the carboxylic acid and acid halide preferably is conducted in an aprotic (dipolar or nonpolar) solvent where, for example, the solvent chosen is acetonitrile, then it is preferably from about 0.1 molar to about 1.5 molar. Suitable solvents are aliphatic or aromatic hydrocarbons, hydrogenated aliphatic or aromatic hydrocarbons, cycloalkanes, dialkylamides, cyclic dialkylamides, ethers, cyclic ethers, polyethers, cyclic polyethers, alkyl nitriles, dialkyl ketones, and the like. The order of addition of the carboxylic acid and acid halide starting materials is not critical; however, in a preferred embodiment the third necessary component for the method, that is phenol, is included with the carboxylic acid and acid halide. As will be understood from the discussion concerning possible Y and/or Z substituents in the Formula I structure, the phenol can be substituted or not, but preferably is unsubstituted so as to prepare the particularly preferred phenyl nonanoate reaction product.

Without being bound by theory, we believe that the reaction between carboxylic acid and acid halide forms a mixed anhydride as an activated intermediate that is unstable so that the bond between the carbonyl from the carboxylic acid and the adjacent oxygen tends to cleave preferentially with respect to the bond between that oxygen and the carbonyl from the acid chloride. In preparing alkanyloxy-benzenes in accordance with this invention, particularly where $R_1$ is an 8 carbon alkyl, we have achieved excellent yields (on the order of 80% or greater). We believe this is due to the favorable thermodynamics just described pertaining to bond cleavage of the mixed anhydride, which is then believed to react with more of the carboxylic acid starting component to form a symmetrical anhydride which, in turn, reacts with phenol to form the reaction product. Thus, the unsymmetrical anhydride may be viewed as an activated intermediate.

We prefer that the amounts of acid halide and phenol used in the reaction be about equivalent to each other and be in a slight excess (up to about a 10% molar excess) with respect to the carboxylic acid.

Because of the favorable thermodynamics, the reaction proceeds readily, and thus only mildly elevated temperatures are deemed useful, such as about 70° C. to about 135° C., preferably from about 70° C. to about 100° C. We have found little increase in yield when temperatures above about 80° C. were used and thus although temperatures above 100° C. are feasible, such would not be more useful than lower temperatures.

The following examples are intended to illustrate and not limit the invention. Example 1 illustrates preparation of a particularly preferred activator in accordance with the inventive method, while the multi-part Example 2 illustrates formulations contemplated of using the activators so prepared.

EXAMPLE 1

A solution of 5.00 g (31.6 mmol) of nonanoic acid, 3.93 g (34.76 mmol) of chloroacetyl chloride (CAC), 2.97 g (31.6 mmol) of phenol, and 35 mL of acetonitrile was delivered to a clean, dry, two neck 100 mL round bottom flask fitted with a mechanical stirrer and a reflux condenser. The reaction flask was flushed with nitrogen through a gas inlet at the top of the reflux condenser and placed in an 80° C. oil bath and stirred for 19 hours. The reaction mixture was allowed to cool to room temperature and then vacuum filtered through 30 g of neutral alumina to remove chloroacetic acid. The purified product was then placed on a high vacuum line overnight to remove any residual solvent. Phenyl nonanoate (NOB) was isolated as a faint yellow liquid (6.18 g, 26.37 mmol) in 83% yield. The purity of NOB was determined to be over 97%.

Phenyl esters prepared in accordance with the invention have use in applications such as peroxide moiety activation in bleaching and cleaning applications, as are illustrated by the several parts of Example 2.

EXAMPLE 2A

In one embodiment of the present invention, the phenyl ester described above may be used as a peracid precursor in combination with a nonionic surfactant to form liquid crystals according to the following:

| Ingredient | Wt. % |
|---|---|
| Phenyl nonanoate | 5.0 |
| Neodol 91-6 surfactant | 25.0 |
| Brine (7.0% NaCl in deionized water) | 70.0 |

EXAMPLE 2B

In this example, a microemulsion of the phenyl ester described above was prepared and used as peracid precursor:

| Ingredient | Weight | Wt. % |
|---|---|---|
| Phenyl nonanoate | 0.515 | 4.95 |
| Ethoxy CO-25 | 1.094 | 10.52 |
| 1.65% NaCl brine | 8.795 | 84.53 |

The microemulsion showed no significant visual changes from about 0° C. to about 30° C., and no separation of components at temperatures of up to about 50° C.

EXAMPLE 2C

This example provides an instance of a macroemulsion colloidal dispersion which may be prepared fro a peroxide precursor, namely, an alkanoyloxybenzene compound. In this instance, NOB is used.

| Ingredient | Wt. % |
|---|---|
| Water | 89.7 |
| Ethoxy HCO-25 | 3.0 |
| Ethoxy CO-200 | 0.5 |
| Phenyl nonanoate | 5.0 |
| $H_2O_2$ | 1.8 |

EXAMPLE 2D

The following formulation provides an example of a oil-core vesicle colloidal dispersion which may be prepared from a peroxide precursor, namely, an alkanoyloxybenzene compound. In this instance, NOB is used.

| Ingredient | Wt. % |
|---|---|
| Water | 90.7 |
| NOVASOME surfactant vesicles[1] | 2.5 |
| Phenyl nonanoate | 5.0 |
| $H_2O_2$ | 1.75 |

[1]Unknown surfactant formulation of third party (Micro Vesicular Systems, Inc.) containing 20% surfactant and lipid materials in water.

The above subparts A–D of Example 2 illustrate preparation of stable peracid precursor-containing liquid colloidal dispersions for use in delivering a peroxyacid to a wash application. The colloidal dispersions may furthermore be formulated as part of a dual delivery system, such as by dispensing separately metered amounts of activators (in some non-reactive fluid medium) and liquid hydrogen peroxide in a container such as is described in Beacham et al., U.S. Pat. No. 4,585,150, issued Apr. 29, 1986. Such a dual bottle is contemplated particularly for applications such as hard surface cleaners.

It is to be understood that while the invention has been described above in conjunction with preferred specific embodiments, the description and examples are intended to illustrate and not limit the scope of the invention, which is defined by the scope of the appended claims.

It is claimed:

1. A method of preparing a phenyl ester, comprising:
    reacting an aliphatic or aromatic carboxylic acid having the structure $$R_1-\overset{O}{\underset{\|}{C}}-OH$$

where $R_1$ is $C_{1-20}$ alkyl or alkenyl or an aryl, with an acid halide having the structure $$A-CH_2-\overset{O}{\underset{\|}{C}}-B$$

where A is a halide, methoxy, ethoxy, or an electron withdrawing group having an O, N, or S heteroatom and B is a halide, to form an activated intermediate; and,
    exposing the activated intermediate to a phenol to form a phenyl ester having the structure $$R_1-\overset{O}{\underset{\|}{C}}-O-\underset{\underset{Z}{|}}{\overset{\overset{Y}{|}}{\phi}} \quad \text{FORMULA I}$$

where Y and Z are each H, $SO_3M$, $CO_2M$, $SO_4M$, OH, a halo substituent, $-OR^2$, $R^3$, $NR_3{}^4X$, and mixtures thereof, wherein M is an alkali metal or alkaline earth counterion, $R^2$ of the $OR^2$ substituent is $C_{1-30}$ alkyl, $R^3$ is $C_{1-6}$ alkyl, $R^4$ of the $NR_3{}^4$ substituent is $C_{1-30}$ alkyl, X is a counterion, and Y and Z can be the same or different.

2. The method as in claim 1 wherein the carboxylic acid and acid halide are reacted in the presence of the phenol.

3. The method as in claim 2 wherein the reaction is conducted in an aprotic solvent.

4. The method as in claim 2 wherein the reaction is conducted at a mildly elevated temperature.

5. The method as in claim 1 wherein the acid halide is from about a 1:1 to about 1.1:1 molar ratio with respect to the carboxylic acid.

6. The method as in claim 1 wherein the acid halide is chloroacetyl chloride.

7. The method as in claim 1 wherein the phenol is substituted or unsubstituted.

8. The method as in claim 7 wherein the phenol is unsubstituted and the phenyl ester reaction product has the structure $$R_1-\overset{O}{\underset{\|}{C}}-O-\phi.$$

9. The method as in claim 1 wherein $R_1$ is $C_{2-18}$ alkyl and further comprises isolating the phenyl ester reaction product in high yield.

10. A method of forming an alkanyloxybenzene comprising:

providing a reaction mixture in an aprotic solvent, the reaction mixture having a linear alkyl $C_{2-12}$ carboxylic acid, phenol and chloroactyl chloride admixed therein;

heating the reaction mixture to between about 70° C. to about 135°; and, isolating an alkanyloxybenzene reaction product having the structure

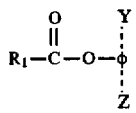

FORMULA I where $R_1$ is $C_{2-12}$ alkyl, Y and Z are each H, $SO_3M$, $CO_2M$, $SO_4M$, OH, a halo substituent, $-OR^2$, $R^3$ $NR_3^4 X$ and mixtures thereof, wherein M is an alkali metal or alkaline earth counterion, $R^2$ of the $OR^2$ substituent is $C_{1-20}$ alkyl, $R^3$ is $C_{1-6}$ alkyl, $R^4$ of the $NR_3^4$ substituent is $C_{1-30}$ alkyl, X is a counterion, and Y and Z can be the same or different.

11. The method as in claim 10 wherein the carboxylic acid is nonanoic acid.

12. The method as in claim 11 wherein the reaction product is phenyl nonanoate.

13. The method as in claim 12 wherein the phenyl nonanoate is isolated in greater than about 80% yield.

14. The method as in claim 12 wherein the solvent includes from about 0.1M to about 1.5M acetonitrile.

15. The method as in claim 10 wherein the phenol and chloroacetyl chloride are each in a minor molar excess with respect to the carboxylic acid.

* * * * *

UNITED STATES PATENT AND TRADEMARK OFFICE
CERTIFICATE OF CORRECTION

PATENT NO. : 5,710,296
DATED : January 20, 1998
INVENTOR(S) : Lafayette D. Foland et al.

It is certified that error appears in the above-indentified patent and that said Letters Patent is hereby corrected as shown below:

In Column 3, line 21, under Detailed Description:

delete the word "incorporated"

sentence should read --in U.S. Pat. No. 5,391,812, wherein Y and Z--

In Column 6, line 42, under Claim 1:

replace "substituent is $C_{1-30}$ alkyl" with:

--substituent is $C_{1-20}$ alkyl--

Signed and Sealed this

Eighth Day of December, 1998

Attest:

BRUCE LEHMAN

*Attesting Officer*  *Commissioner of Patents and Trademarks*